United States Patent [19]

Hsueh

[11] Patent Number: 4,788,848
[45] Date of Patent: Dec. 6, 1988

[54] CHEMICAL TRACER DETERMINATION OF STEAM QUALITY

[75] Inventor: Liming Hsueh, Buena Park, Calif.

[73] Assignee: Chevron Research Company, San Francisco, Calif.

[21] Appl. No.: 135,116

[22] Filed: Dec. 18, 1987

Related U.S. Application Data

[63] Continuation-in-part of Ser. No. 850,203, Apr. 10, 1986, abandoned.

[51] Int. Cl.$^4$ .................. G01N 31/00; E21B 47/00
[52] U.S. Cl. ........................... 73/29; 166/250; 166/252
[58] Field of Search ............... 73/155, 129, 29; 166/264, 250, 252; 250/259, 260

[56] References Cited

U.S. PATENT DOCUMENTS

| | | | |
|---|---|---|---|
| 2,868,625 | 1/1959 | Frank | 73/155 |
| 3,112,182 | 11/1963 | Brown | 73/155 |
| 3,343,408 | 9/1967 | Mayer, Jr. | 73/155 |
| 3,413,838 | 12/1983 | Duddy | 73/29 |
| 3,499,488 | 3/1970 | Haynes, Jr. et al. | 166/250 |
| 4,060,129 | 11/1977 | Gomaa et al. | 166/252 |
| 4,223,727 | 9/1980 | Sustek, Jr. et al. | 73/155 |
| 4,409,825 | 10/1983 | Martin et al. | 73/155 |

*Primary Examiner*—Stewart J. Levy
*Assistant Examiner*—Robert R. Raevis
*Attorney, Agent, or Firm*—S. R. La Paglia; E. J. Keeling; E. A. Schaal

[57] ABSTRACT

A method and means for determining the quality of steam in a flowing steam line is disclosed. A tracer solution is injected into a steam flow line. The tracer solution contains a liquid tracer that will reside almost entirely in the liquid phase and a vapor tracer that will reside almost entirely in the vapor phase in the steam line. Downstream of the tracer injection point a liquid sample and a vapor sample are removed and the concentration of liquid and vapor tracers are determined. With simple mass balance equations the steam quality is then determined.

12 Claims, 1 Drawing Sheet

CHEMICAL TRACER DETERMINATION OF STEAM QUALITY

This is a continuation-in-part of application Ser. No. 850,203, filed Apr. 10, 1986, and now abandoned.

FIELD OF THE INVENTION

This invention relates to a method and apparatus used to determine the ratio of vapor to liquid in two phase flow. More specifically, the invention provides a simple and accurate method of determining the quality of steam flowing in a line with chemical tracers.

BACKGROUND OF THE INVENTION

In the operation of oil field steam flooding operations, wet steam, i.e., steam that contains water in both the liquid and vapor state is frequently injected into oil wells. The mass ratio of vapor to the sum of vapor plus liquid mass in steam is commonly referred to the "quality" of the steam.

In order to efficiently produce an oil field it is necessary to know and control the quality of steam which is being injected into the wells. Steam quality will influence the rate at which oil is produced and the ultimate recovery of the field. As a result, the economics of a field can be greatly affected by the quality of steam being injected into the ground.

Many methods have been proposed to determine the quality of steam used in injection wells. For example, in U.S. Pat. Nos. 3,499,488; 3,596,516 and 3,550,849 a side stream of steam is removed from the main line through an orifice, the liquid is removed, and the salt concentration in the liquid is determined. When the salt concentration of the feedwater is known, a set of equations relating to the steam quality and salt concentrations are solved. This method suffers from a major limitation in that the method is applicale only for a single generator connected to a single injection well. Frequently, a single steam generator will be connected to many injection wells and the steam quality at an individual well is not the same as that of the composite stream.

Another method of determining steam quality involves the use of radioactive tracers, "ASME Steam Turbine Code Test Using Radioactive Tracers", ASME Paper No. 72-WA/PTC-1.

Other methods of determining steam quality require that elaborate equipment be installed in the field. For example, see U.S. Pat. No. 4,135,387 uses acoustic equipment to disperse the phases and then measures the uniformly dispersed phase with acoustic velocity determinations.

Still other methods utilize a dual orifice meter method (for example, see U.S. Pat. No. 4,149,403, assigned to the same assignee as the present invention). These methods are useful only when the steam quality is above 50% and the accuracy of the method is about ±10%.

From the above, it can be seen that an accurate, safe method of determining the quality of steam in a flowing line is needed which does not require elaborate equipment. Consequently, it is an object of this invention to provide a method and means for determining steam quality which is highly accurate. It is a further object of the invention to provide a method and means for determining steam quality in which the field equipment necessary to make these determinations is relatively simple. Another object of the invention is to provide a safe means for determining the quality of steam in a flowing line. Another object of the invention is to provide a method and means in which steam quality can be measured in many wells served by a single generator. Another object of the invention is to provide a method and means in which steam quality can accurately be determined in low quality streams.

SUMMARY OF THE INVENTION

Generally speaking, the invention is designed to accurately and simply provide a means for determining the quality of steam in a flowing line. A metered chemical injection pump injects a known volume of an aqueous chemical containing two tracer components of known concentration. The chemical tracers are selected so that at the pressure and temperature of the steam line, one component will reside substantially in the aqueous phase and one component will reside substantially in the vapor phase.

Downstream of the injection point, at a distance sufficient to allow complete mixing of the injected material, a sample of the liquid pase and vapor phase are extracted in a liquid and vapor trap, respectively. The streams are separately cooled and the vapor stream is condensed. The concentration of chemical tracers are then determined by standard chemical analyses. By using simple mass balance equations, the quality of the steam can then be readily determined.

In one embodiment, the chemical tracer in the vapor phase is an irradiated inert gas. That inert gas does not condense at ambient temperatures and pressures, so the concentration of that inert gas in the vapor phase must be measured by other means, such as with a gamma ray detector.

DETAILED DESCRIPTION OF THE INVENTION

Figure 1:
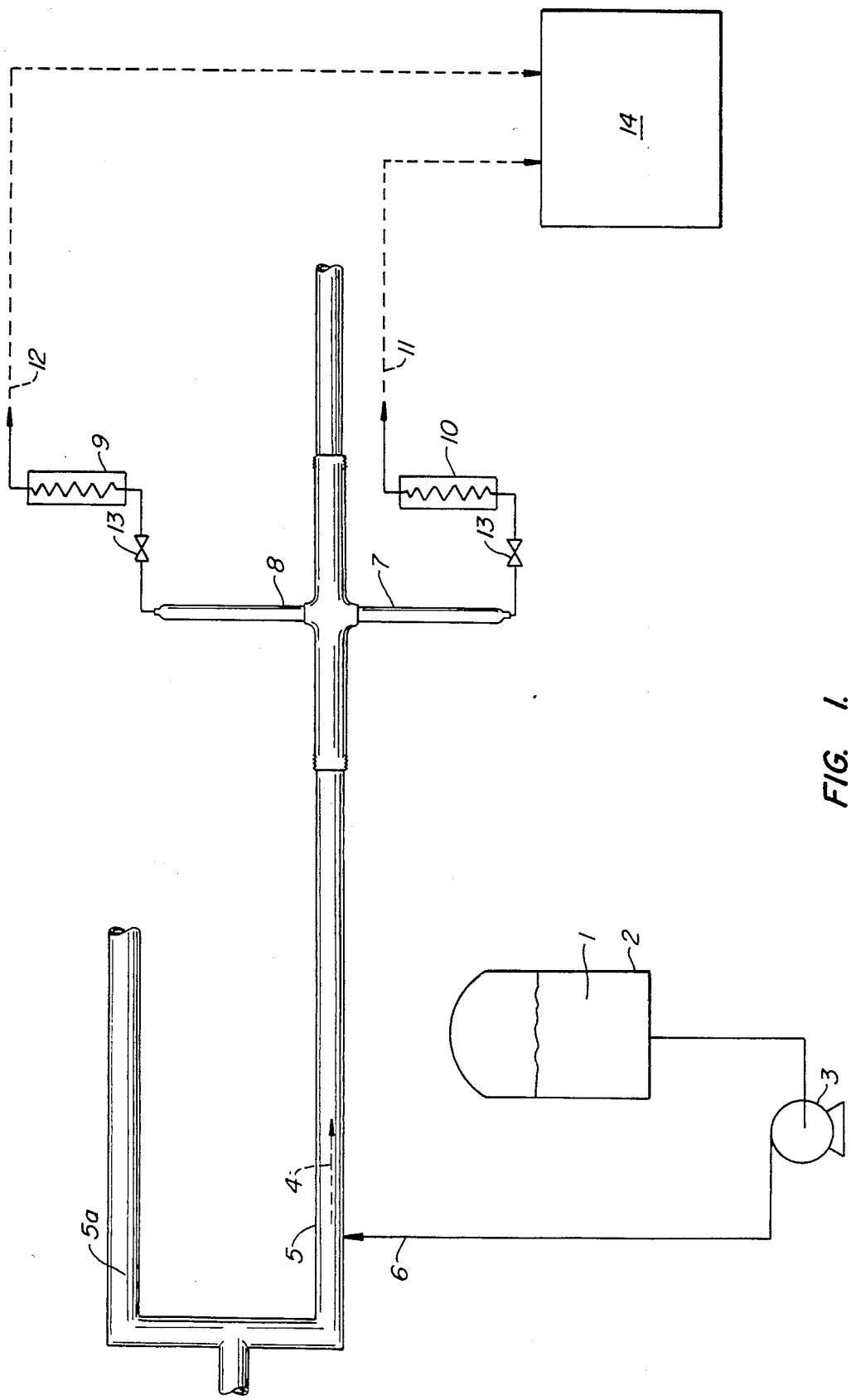
FIG. 1 is a schematic diagram of the chemical tracer method of determining steam quality.

The method and means for determining the quality of steam in a flowing stream is illustrated graphically in FIG. 1. An aqueous solution of vapor and liquid phase tracers 1 is stored in a storage reservoir 2. The tracer chemicals are accurately and precisely measured so that the concentration of the chemicals in the solution will be accurately and precisely known.

The chemical tracers are chosen using the following criteria:

1. The vapor phase tracer must vaporize at the pressure and temperature present in the pipeline, and condense at ambient temperatures and pressures.

2. The liquid phase tracer must reside substantially in the liquid phase at the pressure and temperature conditions in the pipeline.

3. The chemicals must both be stable at the pressure and temperature conditions present in the pipeline.

4. The chemicals must not react with the materials from which the pipeline is constructed (typically carbon steel).

5. The chemicals should be easily analyzable with good accuracy (i.e., ±3%), and preferably analyzable in the field.

6. The chemicals should not pose environmental or safety hazards.

In the preferred embodiment of the invention the liquid phase tracer is a bromide, nitrate, zinc or cobalt solution and the vapor phase tracer is ammonium, aldehyde or a ketone. Obviously, many other tracers could be used. Table I lists other possible tracer candidates.

TABLE I
TRACER CANDIDATES

| Cations | Anions |
|---|---|
| Inorganics | |
| Ammonium (V) | Bromide (L) |
| Zinc (L) | Thiocynate (V, L) |
| Nickel (L) | Nitrate (L) |
| Cobalt (L) | Phosphate (L) |
| Potassium (L) | Floride (L) |
| Boron (L) | Acetate (L) |
| Copper (L) | Iodide (L, V) |
| Manganese (L) | |
| Lead (L) | |
| Titanium (L) | |
| Organics (Water Solubles) | |
| Aldehydes (V) | |
| Ketones (V) | |
| Acids (V) | |
| Alcohols (V) | |
| Amines (V) | |

V = Vapor phase tracer
L = Liquid phase tracer

While the tracer solution is preferably single-phase (liquid) at ambient temperatures and pressures, inone embodiment the tracer solution has both a liquid phase and a vapor phase at ambient temperatures and pressures. In that embodiment, the vapor phase tracer is selected from the group consisting of irradiated Argon, irradiated Krypton, and irradiated Xenon. More specifically, the vapor phase tracer is Krypton 85, Argon, Xenon 133, or other irradiated, thermally stable gases.

The aqueous tracer solution is pumped by means of a metering pump 3 of the type commonly known in the art at a high enough rate such that analyzable tracer concentrations in the liquid and vapor traps are produced (discussed below) and at a low enough rate such that the quality of the steam 4 in the steam flow 4 will not be significantly affected. For 80% quality steam, it would be desirable to inject approximately 500 ppm of aqueous tracer solution at a rate of approximately 500 cc/min into a steam line, although the optimum rate will vary from one situation to the next depending on the steam quality, steam flow rate, the type and concentration of tracers used and other factors obvious to one skilled in the art.

Downstream of the tracer line inlet 6, a liquid trap 7 and vapor trap 8 of the type commonly known in the art are installed. The distance from the tracer inlet 6 to the liquid trap 7 and vapor trap 8 must be adequate to allow the tracer solution 1 to become well mixed with the steam 4. This distance will vary depending on the size of the flow line 5, and the rate at which steam 4 is passing through the line. For a typical oil-field steam line it has been estimated that this distance should be at least 20 feet.

The liquid trap 7 and vapor trap 8 are connected to a vapor condenser/cooler 9 and a liquid cooler 10. Sufficient amounts of liquid are collected for accurate analysis. The concentrations of vapor tracer in the condensed vapor sample 12 and liquid tracer in the liquid sample 11 are then accurately determined by analytical techniques well known to one in the art. This can be done with analytical means 14 connected to the sample lines or by a laboratory at a remote location.

Block valves 13 are provided to open/close the sample lines.

The following procedure can now be used to determine the steam quality. Let:
subscript 1 indicate chemical tracer for liquid phase
subscript 2 indicate chemical tracer for vapor phase
$q$ = the injection rate of tracer solution 1
$Q_1$ = the flow rate of liquid in the stream 4
$Q_v$ = the flow rate of vapor in the stream 4
$c_1$ = the concentration of liquid tracer in solution 1
$c_2$ = the concentration of vapor tracer in solution 1
$L_1$ = the concentration of liquid tracer in stream 11
$L_2$ = the concentration of vapor tracer in stream 11
$V_1$ = the concentration of liquid tracer in stream 12
$V_2$ = the concentration of vapor tracer in stream 12
$X$ = the steam quality of stream 4
Material Balance $$c_1 q = L_1 Q_1 + V_1 Q_v \quad (1)$$

$$c_2 q = L_2 Q_1 + V_2 Q_v \quad (2)$$

$$X = \frac{Q_v}{Q_1 + Q_v} = \frac{1}{1 + \frac{Q_1}{Q_v}} \quad (3)$$

Solve equations (1) and (2) simultaneously $$Q_1 = \frac{c_1 q V_2 - c_2 q V_1}{L_1 V_2 - L_2 V_1} \quad (4)$$

$$Q_v = \frac{c_2 q L_1 - c_1 q L_2}{L_1 V_2 - L_2 V_1}$$

or $\frac{Q_1}{Q_v} = \frac{c_1 V_2 - c_2 V_1}{c_2 L_1 - c_1 L_2}$

Substitute into equation (3)

$$X = \frac{1}{1 + \frac{c_1 V_2 - c_2 V_1}{c_2 L_1 - c_1 L_2}} \quad (5)$$

If substantially all liquid tracer remain in liquid fraction (stream 11) of steam, $c_2 V_1 = 0$ If substantially all vapor tracer goes to the vapor fraction (stream 12) of steam, $c_2 L_2 = 0$
then equation (5) reduces to $$X = \frac{1}{1 + \frac{c_1 V_2}{c_2 L_1}}.$$

Since the concentration of the tracers are known in the vapor sample, the liquid sample, and in the tracer solution, the steam quality can readily be determined.

While particular embodiments of the invention have been described above, this is not to be taken as in any way limiting the invention but merely as being descriptive thereof. For example, the apparatus and method discussed above could be used to measure the ratio of liquid to vapor in flowing lines containing materials other than steam. The invention is not to be limited to such embodiments, but rather by the appended claims.

What is claimed is:

1. Apparatus for determining the quality of saturated steam in a steam line of a multiple-line system served by a single steam generation, said apparatus comprising:
   means for injecting a tracer solution into said steam line at an injection point, said steam line operating at a pressure and temperature and containing a liquid and vapor phase of steam, said tracer solution containing an input concentration of a liquid tracer and an input concentration of a vapor tracer;

means for gathering a vapor sample downstream of said injection point;

means for gathering a liquid sample downstream of said injection point;

means for measuring a concentration of vapor tracer in said vapor sample;

means for measuring a concentration of liquid tracer in said liquid sample.

2. Apparatus as recited in claim 1 wherein:
said vapor tracer is a chemical which resides substantially in said vapor phase at said pressure and temperature;
said liquid tracer is a chemical which resides substantially in said liquid phase at said pressure and temperature.

3. Apparatus as recited in claim 2 wherein said vapor sample is condensed in a condenser means.

4. Apparatus as recited in claim 3 wherein said liquid sample is cooled in a liquid cooling means.

5. Apparatus as recited in claim 4 wherein:
said means for gathering a liquid sample is a liquid trap;
said means for gathering a vapor sample is a vapor trap.

6. Apparatus as recited in claim 1 wherein:
said liquid tracer is a chemical ion selected from the group consisting of bromide, nitrate, zinc, or cobalt, and;
said vapor tracer is a chemical selected from the group consisting of ammonium ion, an aldehyde, or a ketone.

7. Apparatus as recited in claim 1 wherein:
said liquid tracer is a chemical ion selected from the group consisting of bromide, nitrate, zinc, cobalt, nickel, potassium, boron, copper, manganese, lead, titanium, thiocynate, phosphate, floride, acetate, or iodide, and;
said vapor tracer is a chemical selected from the group consisting of ammonium ion, an aldehyde, ketone, organic acid, alcohol, or amine.

8. A method for determining the steam quality in a steam line of a multiple-line system served by a single steam generator, said method comprising:
injecting a tracer solution into said steam line at an injection point, said tracer solution containing an inlet concentration of a vapor tracer and an inlet concentration of a liquid tracer;
removing a vapor sample downstream of said injection point;
removing a liquid sample downstream of said injection point;
measuring a concentration of vapor tracer in said vapor sample;
measuring a concentration of liquid tracer in said liquid sample;
determining the steam quality from the equation:

$$X_s = \frac{1}{\frac{c_1 V_2}{c_2 L_1} + 1}$$

where:
$X_s$ = said steam quality
$c_1$ = said inlet concentration of liquid tracer
$L_1$ = said concentration of liquid tracer in said liquid sample
$c_2$ = said inlet concentration of vapor tracer
$V_2$ = said concentration of vapor tracer in said vapor sample.

9. The method as recited in claim 8 wherein:
said liquid tracer is a chemical ion selected from the group consisting of bromide, nitrate, zinc, or cobalt, and;
said vapor tracer is a chemical selected from the group consisting of ammonium ion, an aldehyde, or a ketone.

10. Apparatus for determining the ratio of liquid to vapor in a multi-phasic flowing line of a multiple-line system served by a single generator, said apparatus comprising:
means for injecting a tracer solution into the multi-phasic line at a pressure and temperature, at an injection point, said tracer solution containing an input concentration of liquid tracer and an input concentration of vapor tracer, said liquid tracer being a chemical which is substantially in a liquid phase at said pressure and temperature and said vapor tracer being a chemical which resides substantially in a vapor phase at said pressure and temperature;
means for gathering a vapor sample downstream of said injection point;
means for gathering a liquid sample downstream of said injection point;
means for measuring a concentration of liquid tracer in said liquid sample;
means for measuring a concentration of vapor tracer in said vapor sample.

11. A method of determining the ratio of liquid to vapor plus liquid in a multi-phasic line of a multiple-line system served by a single generator, said method comprising:
injecting a tracer solution into multi-phasic line at a pressure and a temperature, at an injection point, said tracer solution containing an inlet concentration of a vapor tracer and an inlet concentration of a liquid tracer, said liquid tracer being substantially in the liquid phase at said pressure and temperature and said vapor tracer being substantially in a vapor phase at said pressure and temperature;
removing a vapor sample downstream of said injection point;
removing a liquid sample downstream of said injection point;
measuring the concentration of vapor tracer in said vapor sample;
measuring the concentration of liquid tracer in said liquid sample;
determining a ratio of liquid to liquid plus vapor in said multi-phasic line from the equation:

$$X = \frac{1}{\frac{c_1 V_2}{c_2 L_1} + 1}$$

where:
X = said ratio liquid to liquid plus vapor
$c_1$ = said inlet concentration of liquid tracer
$L_1$ = said concentration of liquid tracer in said liquid sample $c_2$ = said inlet concentration of vapor tracer $V_2$ = said concentration of vapor tracer in said vapor sample.

12. Apparatus for determining the quality of saturated steam in a steam line of a multiple-line system served by a single generator, said apparatus comprising:

a tracer reservoir;

a pump, said pump connected to said reservoir and to said steam line at an injection point;

a vapor trap, said vapor trap located downstream of said injection point;

a liquid trap, said liquid trap located downstream of said injection point;

a liquid cooling means connected to said liquid trap;

a vapor cooling and condensing means connected to said vapor trap;

means for measuring a vapor concentration of ammonia, said means for measuring a vapor concentration of ammonia connected to said vapor cooling and condensing means;

means for measuring a liquid concentration of copper ion, said means for measuring a liquid concentration of copper ion connected to said liquid cooling means.

* * * * *